(12) United States Patent
Krespi et al.

(10) Patent No.: US 11,464,567 B2
(45) Date of Patent: *Oct. 11, 2022

(54) DEVICE AND METHODS OF LASER TREATMENT FOR RHINITIS

(71) Applicant: Valam Corporation, New York, NY (US)

(72) Inventors: Yosef Krespi, New York, NY (US); Ron Hadani, Herzeliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/081,994

(22) Filed: Oct. 27, 2020

(65) Prior Publication Data

US 2021/0038312 A1 Feb. 11, 2021

Related U.S. Application Data

(63) Continuation-in-part of application No. 16/895,951, filed on Jun. 8, 2020, now Pat. No. 11,317,970.

(60) Provisional application No. 62/858,425, filed on Jun. 7, 2019.

(51) Int. Cl.
   *A61B 18/28* (2006.01)
   *A61B 18/00* (2006.01)
   *A61B 17/00* (2006.01)

(52) U.S. Cl.
   CPC ...... *A61B 18/28* (2013.01); *A61B 2017/0023* (2013.01); *A61B 2018/00041* (2013.01); *A61B 2018/00327* (2013.01); *A61B 2018/00404* (2013.01); *A61B 2018/00434* (2013.01); *A61B 2018/00577* (2013.01); *A61B 2018/00589* (2013.01); *A61B 2018/00714* (2013.01)

(58) Field of Classification Search
   CPC .......... A61B 18/22; A61B 2018/00327; A61B 2017/00508; A61B 2018/00434; A61B 2018/2244
   See application file for complete search history.

(56) References Cited

U.S. PATENT DOCUMENTS

| | | | |
|---|---|---|---|
| 6,355,032 B1 | 3/2002 | Hovda et al. | |
| 6,416,491 B1 | 7/2002 | Edwards et al. | |
| 7,442,191 B2 | 10/2008 | Hovda et al. | |
| 8,425,457 B2 | 4/2013 | John et al. | |
| 8,747,401 B2 | 6/2014 | Gonzalez et al. | |
| 9,649,144 B2 | 5/2017 | Aluru et al. | |
| 9,833,276 B2 | 12/2017 | Newman | |
| 9,943,361 B2 | 4/2018 | Wolf et al. | |

(Continued)

FOREIGN PATENT DOCUMENTS

| | | |
|---|---|---|
| AU | 2012202103 A1 | 5/2012 |
| EP | 1039862 B1 | 5/2008 |

(Continued)

*Primary Examiner* — Carl H Layno
*Assistant Examiner* — Aya Ziad Bakkar
(74) *Attorney, Agent, or Firm* — Joseph P. Aiena

(57) ABSTRACT

There is provided a process for treatment of rhinitis by diode laser ablation of the posterior nasal nerves. The laser diode delivery device with elongated optic tip is inserted through a patient's nostril and has the length, flexibility and a curvature to reach both above and under the patient's middle turbinate for treatment to both posterior nasal nerves. Skin and tissue temperature is raised to approximately 60-65° C. with the process. Optimal treatment wavelength was found to be approximately 380-450 nanometers with blue lasers.

11 Claims, 19 Drawing Sheets

(56) References Cited

U.S. PATENT DOCUMENTS

| | | |
|---|---|---|
| 10,456,185 B2 | 10/2019 | Wolf et al. |
| 10,470,837 B2 | 11/2019 | Lin et al. |
| 10,492,810 B2 | 12/2019 | Chang et al. |
| 10,575,893 B2 | 3/2020 | Mayse |
| 10,625,073 B2 | 4/2020 | Townley et al. |
| 10,631,925 B2 | 4/2020 | Wolf et al. |
| 11,026,746 B2 | 6/2021 | Townley et al. |
| 2003/0208194 A1 | 11/2003 | Hovda et al. |
| 2007/0005120 A1 | 1/2007 | Villacampa |
| 2010/0057065 A1 | 3/2010 | Krimsky |
| 2016/0045277 A1* | 2/2016 | Lin ................. A61B 90/06 604/500 |
| 2017/0231474 A1 | 8/2017 | Saadat et al. |
| 2018/0103994 A1 | 4/2018 | Fox et al. |
| 2018/0161084 A1 | 6/2018 | Newman |
| 2018/0344411 A1 | 12/2018 | Fahey et al. |

FOREIGN PATENT DOCUMENTS

| | | |
|---|---|---|
| WO | WO1999020185 A1 | 4/1999 |
| WO | WO2015153696 A1 | 10/2015 |

* cited by examiner

| Temperature Deg °C | Visual Change | Biological Change – Soft Tissue |
|---|---|---|
| 37-60 °C | No visual change | Warming Hyperthermia |
| 60-65 °C | Blanching | Coagulation |
| 65-90 °C | White / grey | Denaturation |
| 90-100 °C | Puckering | Drying |
| 100 °C | Smoke plume | Vaporisation |
| >200 °C | Blackening | Blackening |

Laser Tissue Interaction

FIG. 12

Hemoglobin and oxy-hemoglobin absorption spectra, also showing emission lines of KTP laser and blue diode lasers

DEVICE AND METHODS OF LASER TREATMENT FOR RHINITIS

CROSS REFERENCE TO RELATED APPLICATIONS

This application is a continuation in part of U.S. patent application Ser. No. 16/895,951, now U.S. Pat. No. 11,317, 970, filed on Jun. 8, 2020, which claims the benefit of and priority to U.S. Provisional Patent Application No. 62/858, 425 filed on Jun. 7, 2020, each of which are incorporated herein by reference in its entirety.

FIELD OF THE INVENTION

The present invention relates to the field of treatment of rhinitis, and more particularly to the field of laser treatment of rhinitis.

BACKGROUND

Rhinitis is defined as an inflammatory condition that affects the nasal mucosa. Its symptoms include nasal obstruction, hyperirritability, and hypersecretion. Rhinitis can be caused by a variety of different allergic and nonallergic conditions. The prevalence of rhinitis seems to have increased since the industrial revolution. One in five Americans is estimated to be afflicted with rhinitis, totaling about 60 million individuals. Allergic rhinitis is one of the most common chronic conditions in the United States. The symptoms of nonallergic rhinitis include nasal obstruction, hypersecretion, and irritability, none of which are due to allergy. Nonallergic rhinitis can be further subdivided, with vasomotor rhinitis being the most common. The symptoms of vasomotor rhinitis exacerbate with age. Allergic rhinitis may be seasonal, perennial, or both, and is characterized by sneezing, itching, rhinorrhea, and congestion. This study did focus on both allergic and nonallergic rhinitis.

Treatment is initially medical and administered via single or multi-agent, topical, systemic, or combined methods. Agents include saline irrigations, topical steroids, topical or systemic adrenergic agents, antihistamine therapy, anticholinergic agents, antileukotrienes, and combinations of these. Drawbacks include tachyphylaxis, reliable efficacy, and the need for constant daily treatment.

Multiple surgical solutions exist with varying degrees of effectiveness. Vidian neurectomy (VN), first described in 1961, was largely abandoned due to its complexity and complications that included severe bleeding from the sphenopalatine artery (SPA), crusting, cheek and palate numbness, and significant eye dryness. Although VN regained some popularity with the invention of endoscopic techniques, technical limitations with the problem of eye dryness remain present. Posterior nasal nerve (PNN) neurectomy, a modification of VN, appeared as a safer technique due to ophthalmic sparing and the fact that it targets only the posterior nasal nerve branches. Resection of the PNN reflects the physiological elimination of the parasympathetic stimulus to the inferior turbinate as induced by ipratropium, significantly improving both rhinorrhea and nasal obstruction. The induced sensory denervation further reduces secretagogue generation by reducing neurogenic inflammation. PNN resection appears to be a safe procedure that induces apparent histological changes and is sustainable for at least 48 months. Thus, selective resection of PNN can be a successful treatment for allergic and non-allergic rhinitis. PNN resection has been performed through several methods. Meticulous dissection of the SPA allows for identification of the nerve, which is found mostly posterior and inferior to the artery, usually while sparing the artery. Recently developed alternative approach targeting the lateral nasal wall mucosa without any dissection can also be applied. This can be achieved with a cryotherapy device (applied endoscopically to the posterior middle meatus) that is used to freeze the PNN region, bilaterally. Without precise identification of the nerve, cryotherapy can be done in the office, and a follow-up with patients has shown reduction in rhinorrhea and congestion for many months.

SUMMARY OF THE INVENTION

The present invention is a process and device for laser ablation of the posterior nasal nerves (PNN) for the treatment of rhinitis. The laser diode delivery device with elongated optic tip is inserted through a patient's nostril and has an ability to reach both above and under the patient's middle turbinate for treatment of both branches of the posterior nasal nerve. Skin and tissue temperature is raised to approximately 60-65° C. during the treatment process. Optimal treatment wavelength was found to be approximately 940 nanometers with the present invention. In an embodiment, with blue laser and an optimal treatment wavelength of 380-450 nanometers is used with the present invention by placing an optical filter in between the camera and the endoscope connected to the delivery device in the present invention. The blue laser has the ability to have unique temperature feedback control parameters and as a result will temporarily shut off or create pulsing action (on-off) to maintain the tissue temperature constant until the end of the medical procedure. The inclusion of the optical filter avoids scattering of the blue laser beam and allows the surgeon to clearly see the target area.

The process of the present invention for the treatment of rhinitis by laser ablation of posterior nasal nerves includes ablating the posterior nasal nerves by a diode laser delivery device with an elongated uninitiated clear fiber tip. As the posterior nasal nerves are located above and below a middle turbinate of the patient, the diode laser delivery device is initially inserted through the patient's nostril and into an area of tissue near the middle turbinate. In the process of the present invention, the laser diode operates at approximately 940 nanometers. With the process, the heating of tissue by the device is done to approximately 60 to 65 degrees Celsius. The tip of the diode laser delivery device is positioned at a location above the middle turbinate. The process then ablates the lateral posterior superior branches of the posterior nasal nerves. By then positioning the tip of the diode laser delivery device at a position below the middle turbinate, the process allows the medical professional to ablate the lateral posterior inferior branches of the posterior nasal nerves. In an embodiment of the present invention, the fiber tip of the laser delivery device is malleable and is adjustable and capable of configuration to anatomical differences to individual patients. In an embodiment of the present invention, the fiber tip of the laser delivery device is disposable. In another embodiment of the present invention, the laser delivery device is re-usable. The delivery device for the present invention is disposable in another embodiment and the fiber tip is connected to the disposable delivery device by removable means. The delivery device includes a disposable sheath to cover the delivery device in an embodiment.

A diode laser ablation of posterior nasal nerves (PNN) study was performed: Office based (Topical/Local Anesthesia), N=11; Ambulatory (Sedation/General anesthesia), N=21. Based on the results, there were shown: Non-allergic 15 pts (47%), Allergic 17 pts (53%). In ASU, when anatomy does not permit endoscopic access, there is benefit of the present invention. There is the added benefits of short treatment time, it is well tolerated by patients with rapid healing, and no crusting.

The 940 nm diode laser ablation thermal profile is used with the present invention. Using a clear tip fiber in non-contact mode, tissue temperature is raised to 65-70 C max to achieve very superficial mucosal blanching and ablate the PNN traveling just under mucosa. By keeping temperature under 70 C denaturation is achieved, which is partially reversible and may be early coagulation, (never vaporization).

With the present invention the advantages of 940 nm diode laser with clear fiber tip are shown. This wavelength is optimal wavelength for ablating mucosal surface and provides controlled tissue heating. The clear fiber tip in non contact mode blanches the mucosa selectively effecting the nerves in sub-mucosa. There is minimal crusting and swelling with the present invention and provides an improved method for targeting two zones in the back of the nose, targeting the lateral inferior and lateral superior PNNs.

In an embodiment, there is a process for the treatment of rhinitis by laser ablation of posterior nasal nerves which comprises ablating the posterior nasal nerves by a diode laser delivery device with an elongated clear fiber tip, where the posterior nasal nerves are located above and below a middle turbinate. The diode laser delivery device is inserted into an area of tissue near the middle turbinate with the laser diode laser delivery device operating at approximately 380 to 450 nanometers—a blue laser process. The process heats the tissue to approximately 60 to 65 degrees Celsius and then the process positions the tip of the diode laser delivery device at a position above the middle turbinate. The process continues by ablating the lateral posterior superior branches of the posterior nasal nerves and positioning the tip of the diode laser delivery device at a position below the middle turbinate. Then, the process ablates the lateral posterior inferior branches of the posterior nasal nerves.

In an embodiment of the blue laser process, the fiber tip of the diode laser delivery device is malleable. In an embodiment of the process, the fiber tip of the diode laser delivery device is adjustable and capable of configuration to anatomical differences. In another embodiment of the blue laser process, the fiber tip is disposable. In an embodiment of the blue laser process, the diode laser delivery device is re-usable. In yet another embodiment, the diode laser delivery device is disposable. In an embodiment, the fiber tip is connected to the disposable diode laser delivery device by removable means. In another embodiment of the blue laser process, the diode laser delivery device includes a disposable sheath to cover the diode laser delivery device.

The process, in another embodiment, further comprises selectively ablating blood vessels with a blue laser in a non-contact coagulation mode. In an embodiment, the process includes wherein the laser diode delivery device operating at approximately 380 to 450 nanometers further comprises an optical filter placed between a camera and an endoscope which are connected to the laser diode delivery device. In an embodiment, the process the laser diode delivery device includes a GaN diode.

BRIEF DESCRIPTION OF THE DRAWINGS

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 12 is a general reference chart of laser tissue interaction of temperature, visual change and biological change.

DETAILED DESCRIPTION

Figure 1:
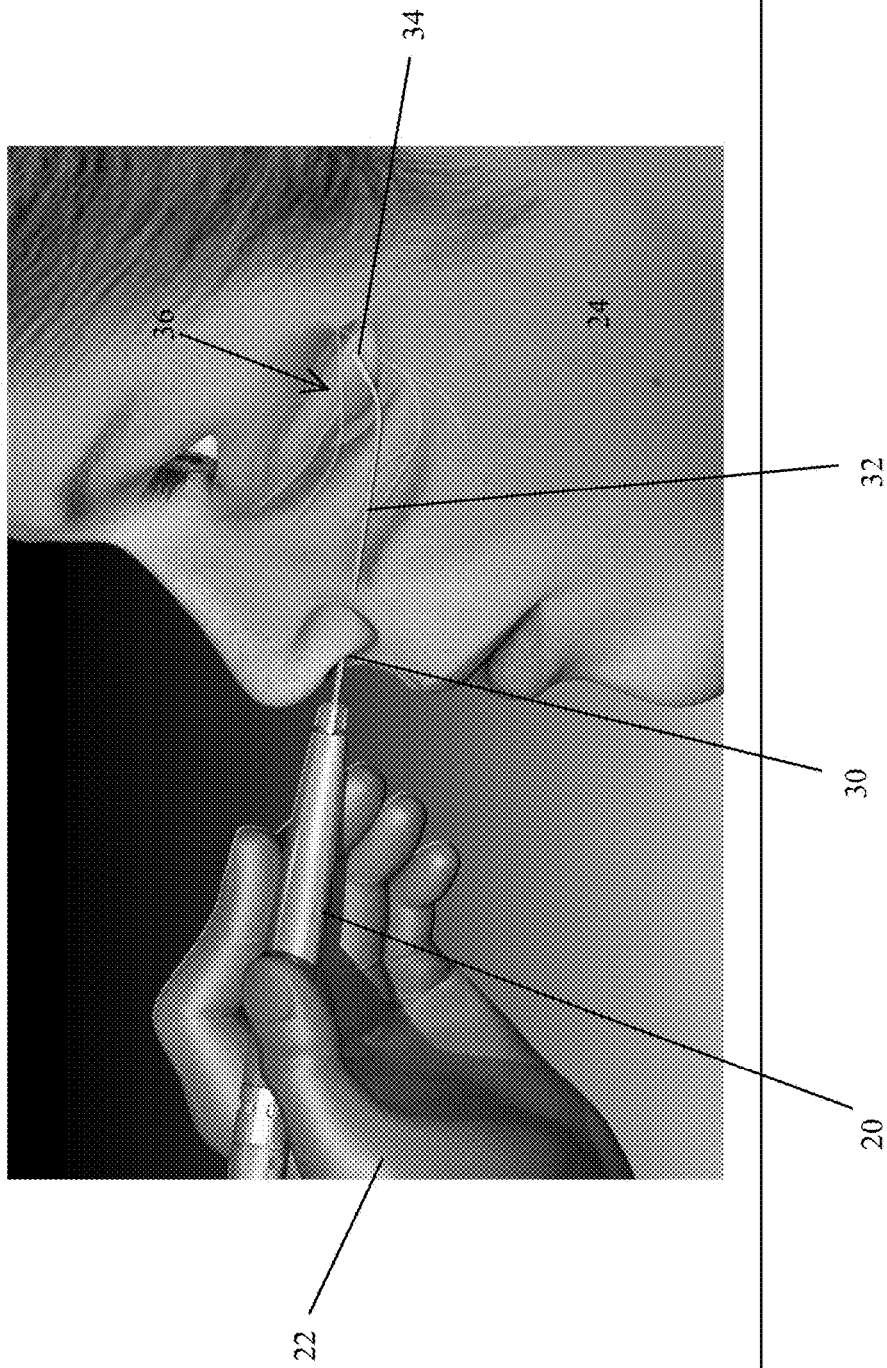
FIG. 1 illustrates a procedure of the present invention.
Figure 2:
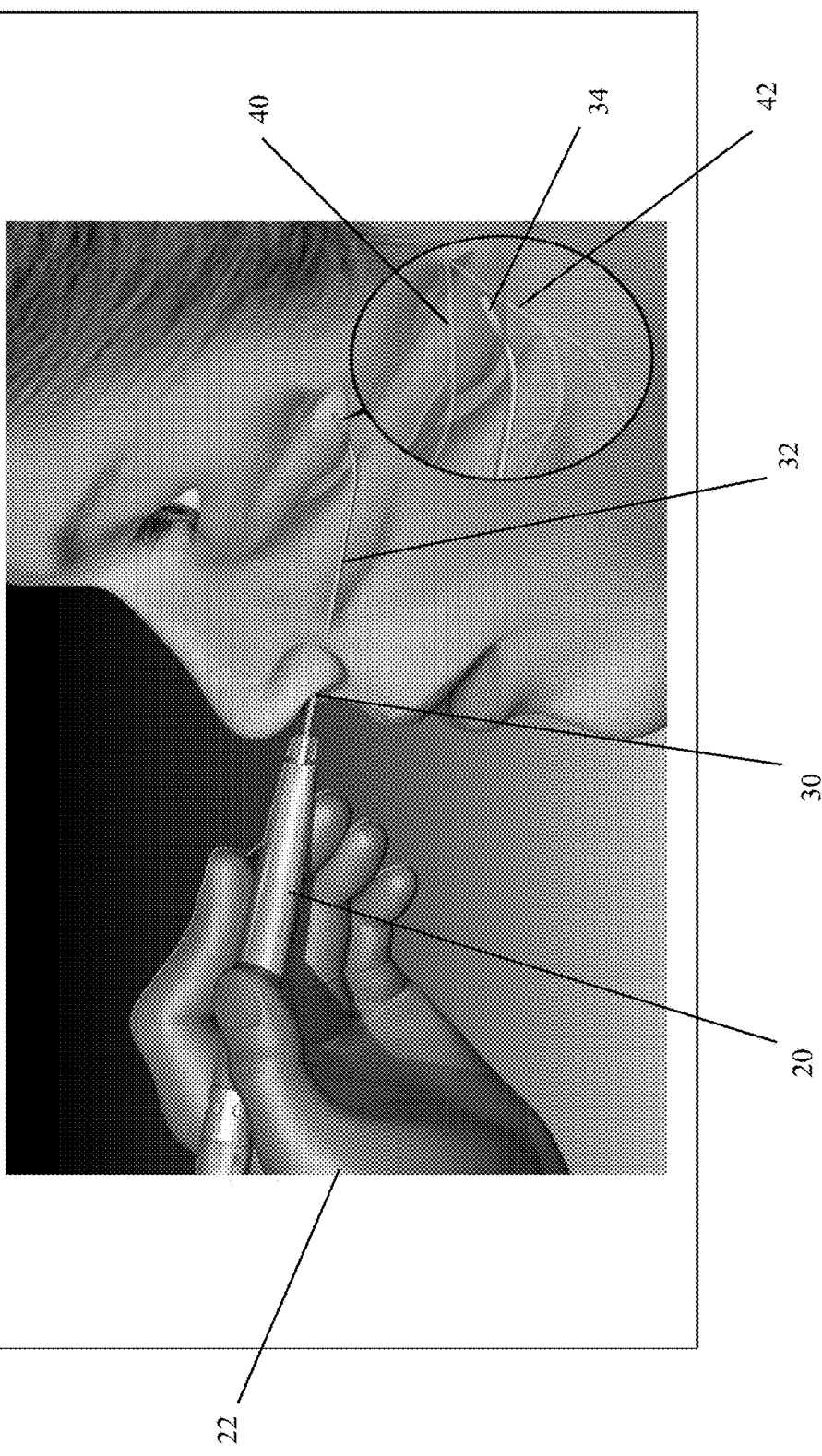
FIG. 2 illustrates a procedure of the present invention with an exploded view.

The present invention shall be described with reference to the included Figures and charts. FIGS. 1 and 2 illustrate the process of treatment of rhinitis. In FIG. 1 there is shown diode laser ablation of posterior nasal nerves (PNN), with the treatment of lateral posterior superior branches of the nerves. The illustration includes a patient 24 and a medical professional 22 holding the diode laser devices 20 for delivery of treatment to the patient. The handheld laser device 20 with elongated and needlelike neck 32 culminating in fiber tip 34 is inserted through the patient's nostril 30 with the tip 34 of the diode laser device extending into the area of the patient's middle turbinate 36. In the area of the middle turbinate, there are two nerves indicated by the set of branched lines extending from a common point. One nerve (superior branch) 40 is located above the middle turbinate and one nerve (inferior branch) 42 is located below the middle turbinate. In FIG. 1, the tip of the diode laser delivery system is above the middle turbinate 36. The lateral posterior superior branches 40 are treated in this manner.

In FIG. 2, the tip of the laser diode is inserted below the middle turbinate 36 and ablation occurs here below the middle turbinate. This is seen in the exploded view of FIG. 2 where the tip 34 of the laser diode is set for treatment delivery below the middle turbinate 36 and to reach the lateral posterior inferior branches 42 of the posterior nasal nerves 40, 42. The laser diode treatment operates at approximately 940 nanometers with skin/tissue temperature raised up to 60 to 65° C. The important goal is to perform the treatment, but not to destroy the tissue. The surface is heated, but no contact.

The laser diode delivery system in this process is able to reach both nerves 40, 42 for treatment, as opposed to cryo-technology treatments which are only able to treat a single nerve due to the size of the device used in cryo-technology treatment processes.

Figure 3:
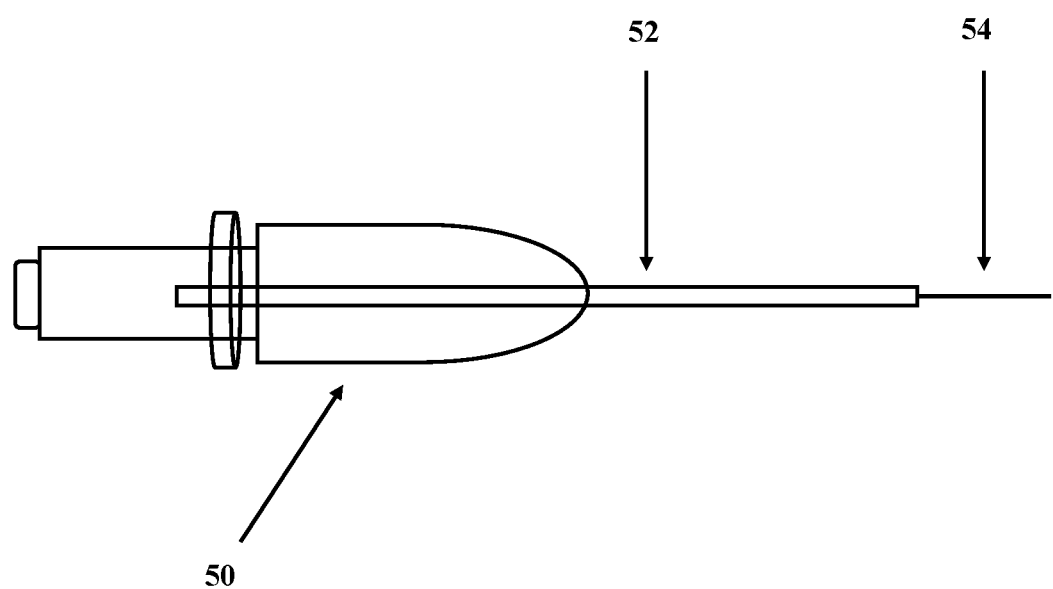
FIG. 3 is the delivery system for use with the present invention.

Referring to FIG. 3, there is shown the laser device 50 and delivery system for use with the present invention. The delivery system has fiber of approximately 1.5 m in a modified coupler to laser with 300 μm core. The elongated fiber design 52 is rigid, yet has sufficient curvature at the tip 54 for positioning and re-positioning by the medical professional without having to withdraw the instrument after insertion for slight location changes (See, FIGS. 1 and 2). It is positioned in contact with tissue surface and generates 4 watt output at the fiber tip. This is with a bare uninitiated fiber tip 54 and should be distinguished from the black tip technique, which is undesirable with the present invention as described below. The black tip technique includes a carbon coating on the tip absorbing 30-50% of laser light at the tip. With the present invention, the fiber tip of the laser delivery device is malleable and or made of a malleable material. The fiber tip of the laser delivery device is adjustable and capable of configuration to anatomical differences for each individual patient. The fiber tip is disposable or alternatively, the delivery device is disposable with the fiber tip connected to the disposable delivery device by removable means, such as fasteners, clips, mechanical methods, adhesives. The delivery device may also include a disposable sheath to cover the delivery device. Re-usable delivery devices are also an embodiment of the present invention.

In order to determine the optimal methods with the present invention, a comparison of laser diode wavelengths 810, 940 and 980 nm for both clear tip and black tip delivery was analyzed. The results provide a visualization of thermal distribution in biological tissues and a comparison effect of tissue chromaphores. The comparison involved tissue with high blood content (dark liver was used) and low blood content (pale pork muscle was used).

Figure 4:
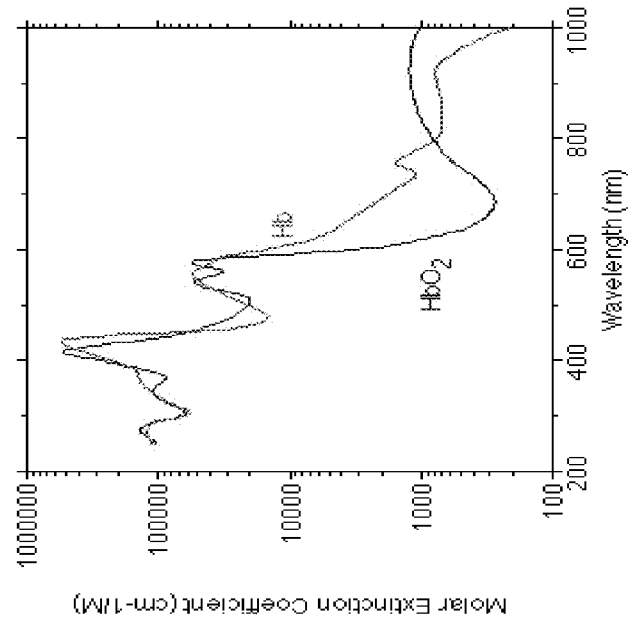
FIG. 4 is a chart of the absorption chromaphores molar extinction coefficient vs. wavelength.
Figure 5:
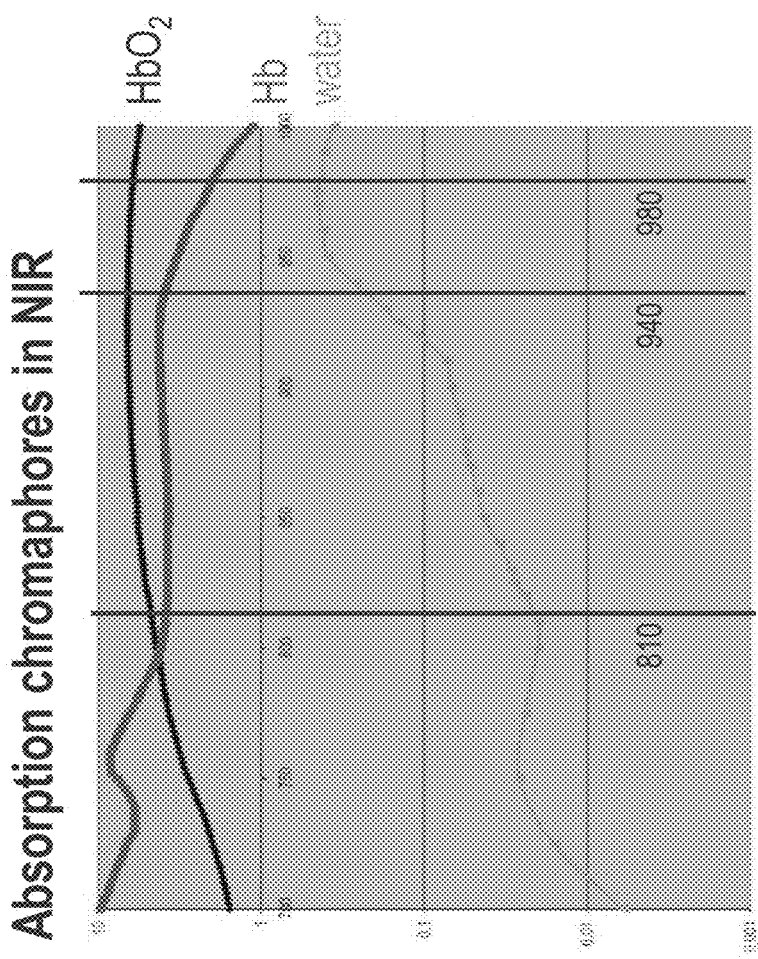
FIG. 5 is a chart of absorption chromaphores in NIR.

FIGS. 4 and 5 illustrate the absorption chromaphores of Hb and $HbO_2$, with the wavelengths of 810 nm, 940 nm and 980 nm indicated in FIG. 5.

Figure 6:
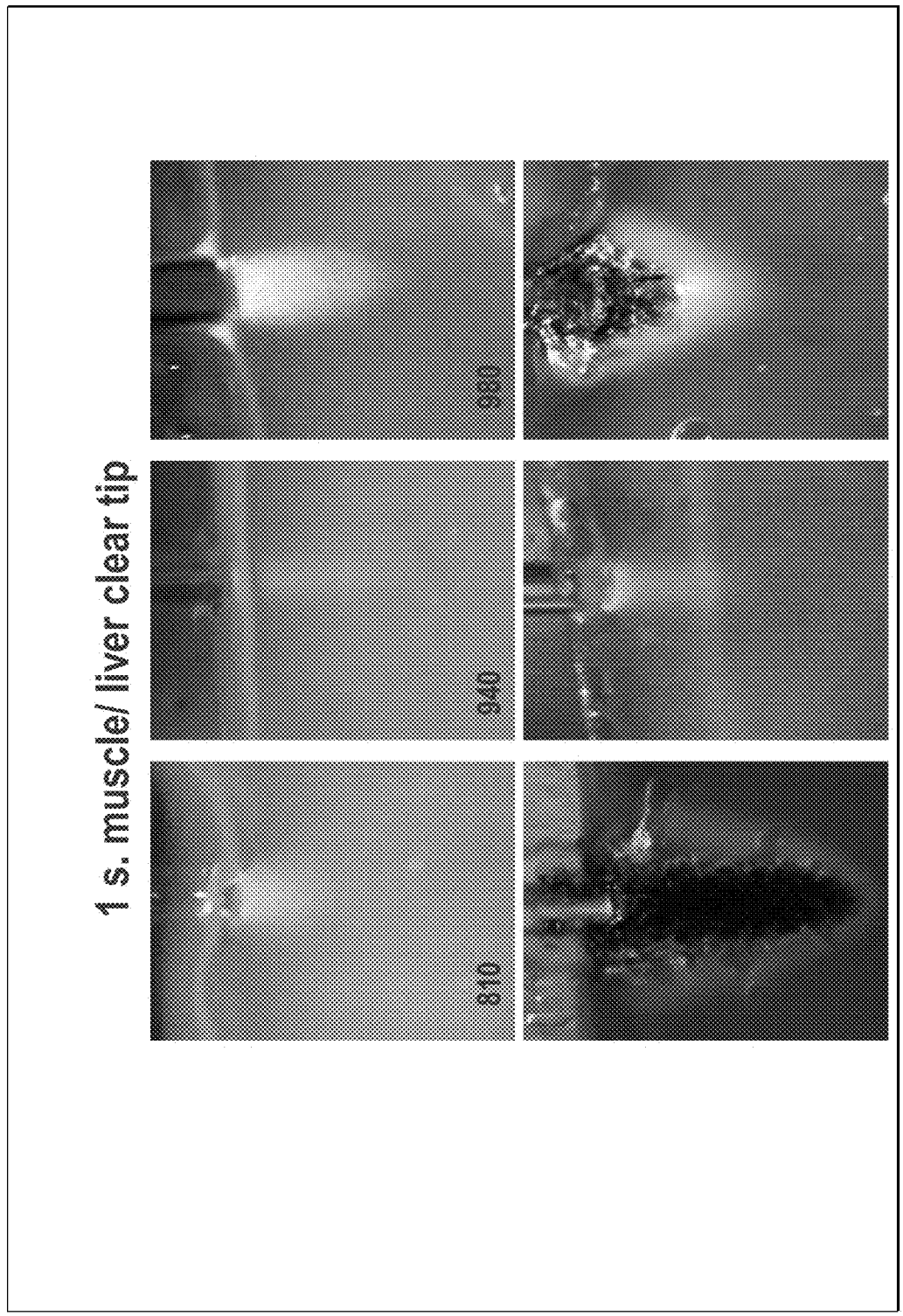
FIG. 6 illustrates 1 second of treatment with clear tip laser device at various wavelengths.
Figure 7:
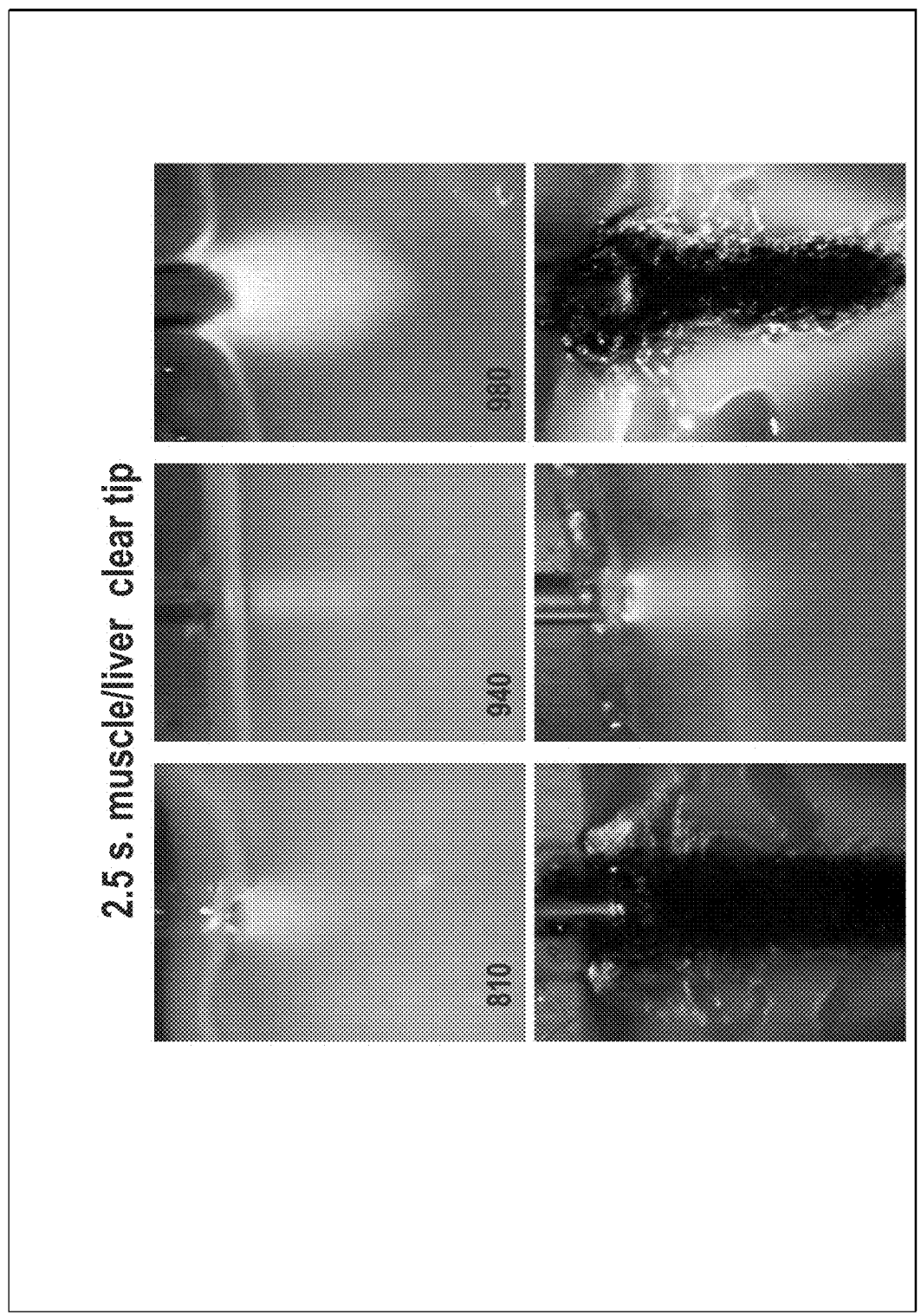
FIG. 7 illustrates 2.5 seconds of treatment with clear tip laser device at various wavelengths.
Figure 8:
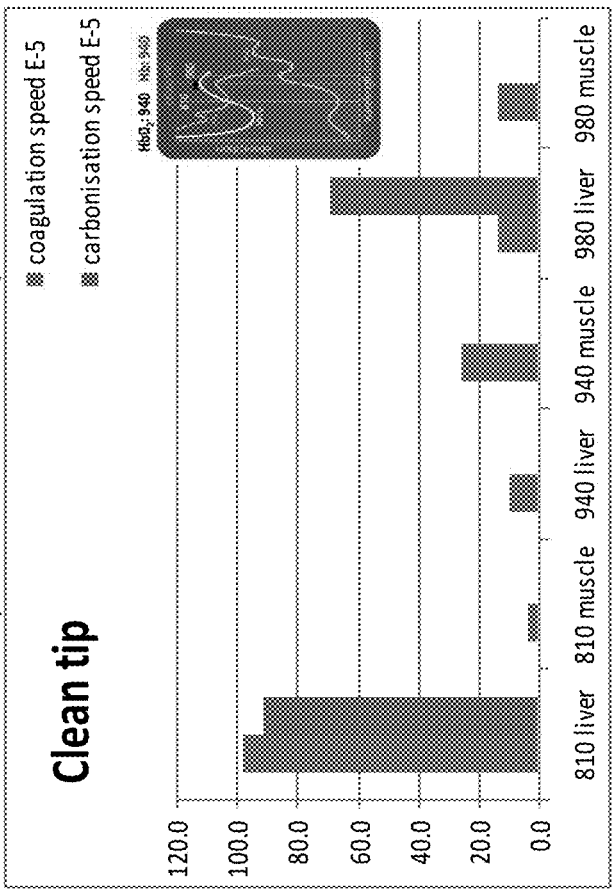
FIG. 8 is a chart of coagulation speed with the clean/clear tip laser device.

With FIGS. 6, 7, and 8, there is shown the effects of the clear tip technique which is used with the present invention. FIG. 6 illustrates one second treatment of muscle tissue (top row) and liver tissue (bottom row) with clear tip treatment. The results are shown for 810, 940 and 980 nm, with 940 nm indicating no destruction of tissue. Similarly, FIG. 7 illustrates 2.5 second treatment of muscle (top row) and liver tissue (bottom row) with a clear tip delivery device. Again, the results are shown for 810, 940 and 980 nm with 940 nm indicating no destruction of tissue. FIG. 8 indicates the coagulation speed with the clean tip for liver and muscle tissue at each of the wavelengths of 810, 940 and 980 nm.

Figure 9:
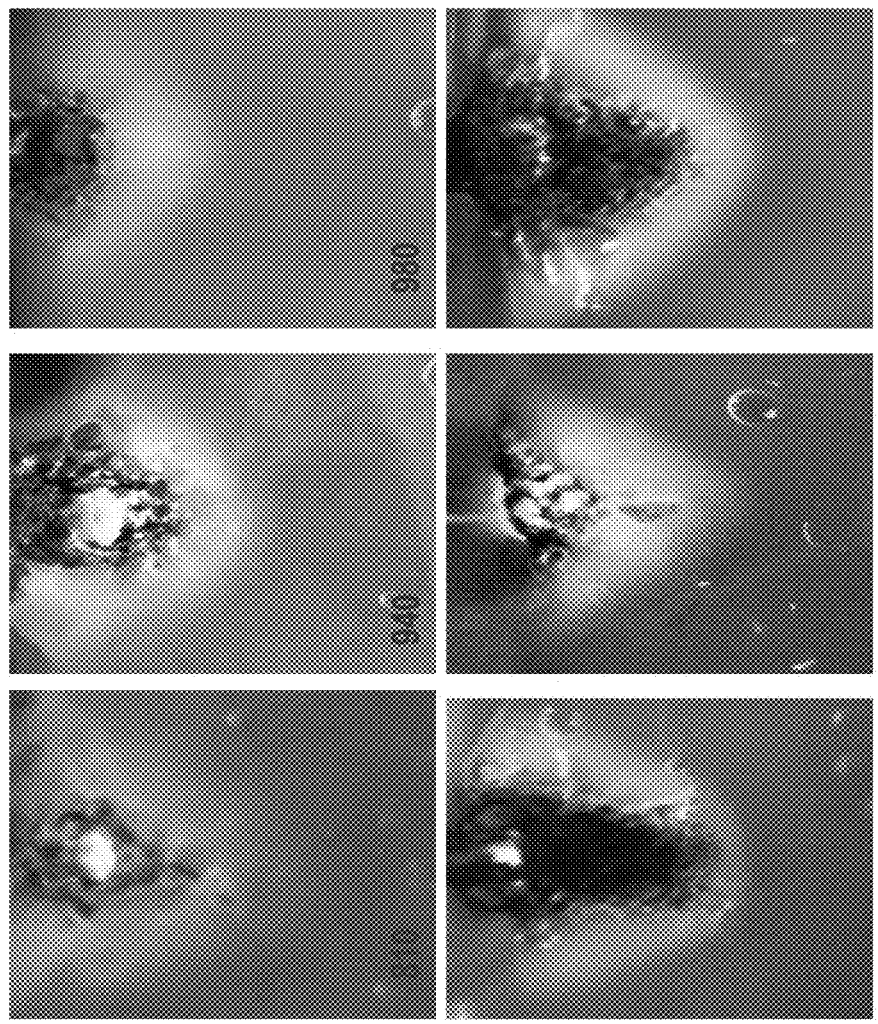
FIG. 9 illustrates 1 second of treatment with a black tip laser device with undesirable results.
Figure 10:
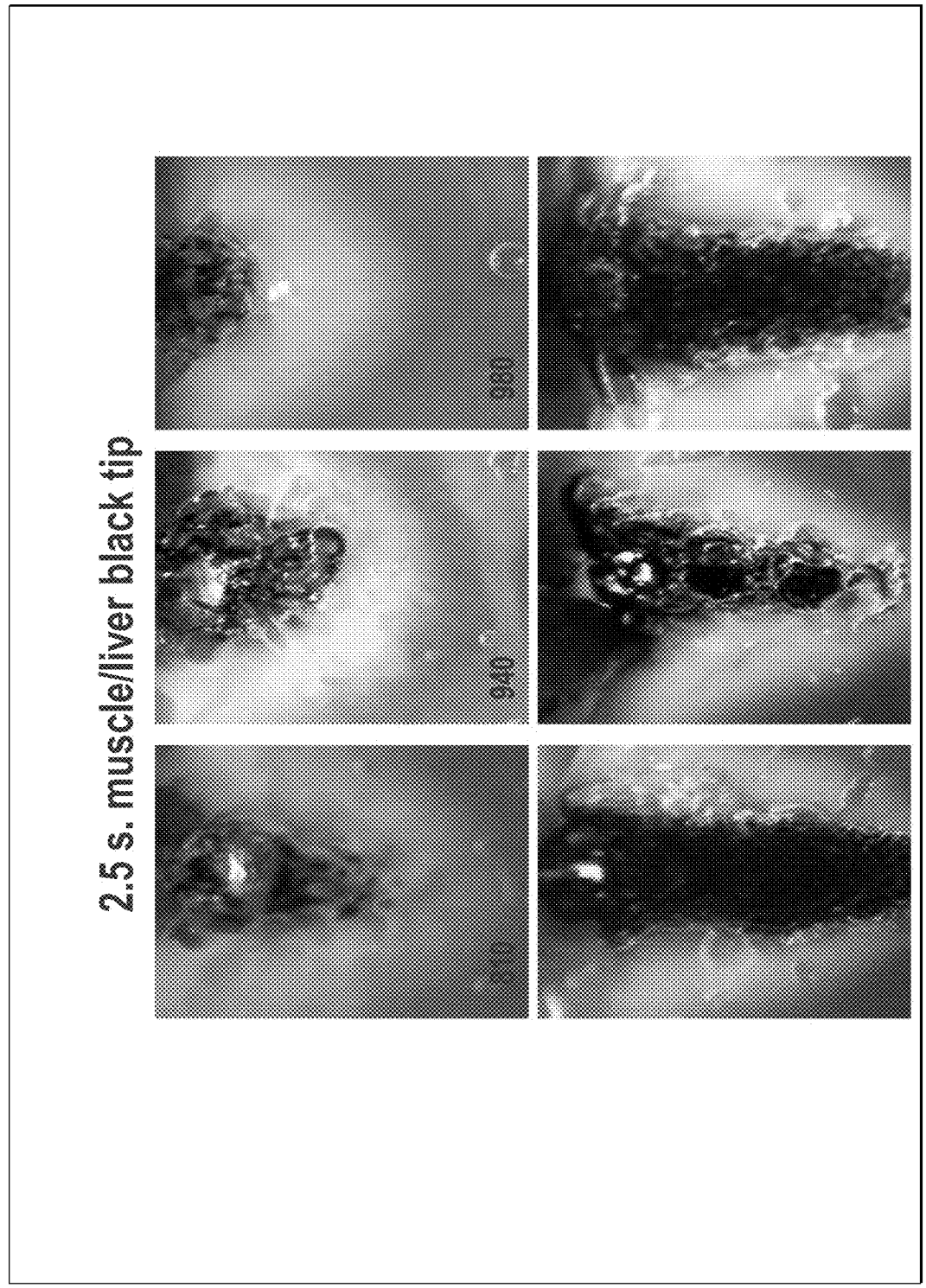
FIG. 10 illustrates 2.5 seconds of treatment with a black tip laser device with undesirable results.
Figure 11:
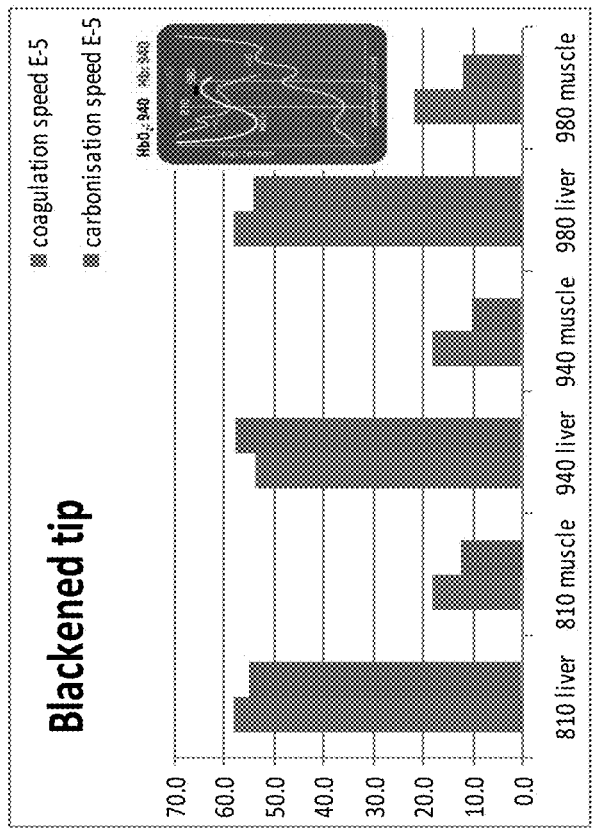
FIG. 11 is a chart of coagulation speed with the black tip laser device.

With FIGS. 9, 10, and 11, there is shown the undesirable effects of the delivery system using the black tip technique as it destroys tissue. This is shown with FIGS. 9 and 10 respectively as images of damaged tissue with 1 second treatment (FIG. 9) and 2.5 seconds treatment (FIG. 10) across a range of wavelengths 810 to 980 nanometers for each treatment. FIG. 11 indicates the coagulation speed with the blackened tip.

The observations are reproducible in series (3 times). The high Hb absorption at 810 nm is higher than theoretical expected as compared to 940 and 980 nm. The tissue effect at 940 nm seems to be less dependent on the presence of chromaphores compared to that at 810 and 980 nm for a controlled coagulation effect. The 940 nm diode laser shows to have a controlled coagulation/sterilization effect less dependent on the presence of blood. For 810 nm and 980 nm diode lasers initiate tissue carbonization and ablation within a few seconds depending on the presence of chromaphores (especially blood). The pre-coated 'black tip' is very efficient for instant ablation of tissue within 1 second.

The 940 nm diode laser has a wavelength allowing for controlled submucosal thermal penetration. The diode laser is used in both vein ligation and neural tissue ablation through a non-contact (not initiated) type tip. As the vessel ablation requires power settings around 12 W, and nerve/brain tissue ablation is induced at 6 W, a power setting of no more than 5-6 W is sufficient for ablating the endonasal nerves. If the laser's heat is maintained above a certain threshold temperature at which proteins begin to denature, the tissue irreversibly coagulates and the tissue's optical properties (most significantly, the absorbance properties) change, usually around 60-80 C level. This is easily monitored by observing the properties of the nasal mucosa, as overheating may produce vaporization and carbonization, at temperatures 100-300 C which are not desired.

Armed with data generated from bench experiments and learning from various disciplines, such as testing diode laser exposure on tissue using clear (non-initiated) and black (initiated) fiber tips with various power densities, the 940 nm laser's potential as a tool in PNN ablation was explored. Overall, it is shown that the laser diode delivery at 940 nm is the best wavelength to ablate and safely coagulate without deep penetration and minimal lateral tissue necrosis. A range of wavelengths around the 940 nm, slightly greater and slightly less similarly provides the results.

The non-contact ablation method with un-initiated fiber tip (Clear tip) at around 4-5 W, gives the best and safe results for superficial tissue ablation.

With the present invention, the following clinical study has been performed:

Clinical Study Overview:

Design Prospective, non-randomized

Population Healthy patients with rhinorrhea and nasal congestion who failed medical therapy Primary Endpoint Total Nasal Symptom Score (TNSS) at Baseline, 30, 90 days post treatment Scoring Scales TNSS, validated symptom scale Four nasal symptoms. Rhinorrhea, Nasal obstruction, Nasal itching, Sneezing 0-3 point scale 0=Absent symptoms 1=Mild symptoms 2=Moderate symptoms 3=Severe symptoms Results: Feasibility and Safety There were 31 patients, with 30 and 90 days follow up received from 30 patients. For feasibility, there was an ability to complete the procedure in 96% of the cases. There were 10 in the office, 21 in the ASU due to anatomical access. Topical and/or local anesthesia was used in the office. The average pain score was 1.8 (scale of 0-10). For safety: there was no laser related events, no bleeding, and no crusting, headaches, facial pain or ear blockage.

Results: Efficacy
Symptoms Score 30 Days:
  55% improvement in TNSS
    Mean score 7.1 (out of 12) at baseline, reduced to 3.2
  48% improvement in Rhinorrhea
    Mean score 2.3 (out of 3) at baseline, reduced to 1.2
  53% improvement in Congestion
    Mean score 2.1 (out of 3) at baseline, reduced to 1.0
Symptoms Score 90 Days:
  51% improvement in TNSS
    Mean score 7.1 (out of 12) at baseline, reduced to 3.5
  44% improvement in Rhinorrhea
    Mean score 2.3 (out of 3) at baseline, reduced to 1.3
  48% improvement in Congestion
    Mean score 2.1 (out of 3) at baseline, reduced to 1.1
Medication Use
  70% reduction in medication use at 90 days
  (Decongestants, antihistamines, steroids, anticholinergics)
  Conclusions
Laser ablation of PNN is a well tolerated, safe, office or ambulatory procedure. Laser ablation of PNN improves both nasal congestion and rhinorrhea, also reduces medication use. Both allergic and non-allergic rhinitis appears to benefit from Laser Ablation of PNN. The results are similar to other treatment modalities. An on going analysis of long term outcomes in much larger series in a multicenter environment are next steps for study.

The Study: Endoscopic, Non-Contact Diode Laser Ablation of the Posterior Nasal Nerve Region in Treating Rhinitis.

Background: Posterior nasal nerve (PNN) surgery, or cryoablation, has been described as an alternative treatment for allergic and vasomotor rhinitis. We hypothesize that endoscopic (diode) laser ablation (ELA) is effective and less invasive than previously described methods.

Methods: The prospective study was performed with approval from the IRB. Thirty-two patients with chronic rhinitis and nasal congestion resistant to medical management were recruited. Total Nasal Symptom Score (TNSS) measurements were used to assess symptom severity and treatment outcomes. ELA was performed in the clinic under topical/local anesthesia in 11 patients, while the remaining 21 were treated under anesthesia in the operating room. The 400 micron uninitiated diode laser fiber tip with a malleable protective shaft was specially designed for PNN ablation. The fiber was pre-shaped according to the intranasal anatomy and endoscopically advanced toward the posterior middle meatus. The ELA method using a 940 nm diode laser at CW 5 W to bilaterally ablate the PNN region. Patients were followed up with for the first at 90 days after treatment.

Results: ELA was successfully completed in 97% of patients. No crusting, epistaxis, or other complications were observed. One patient could not be treated in the office due to limited endoscopic access. TNSS scores were reduced by 55% after 30 and by 51% after 90 days (p<0.001). Rhinitis and congestion scores were also decreased at 90 days by 44% and 48% respectively after treatment compared to the baseline (p<0.001).

Conclusion: ELA of the PNN region is safe and well tolerated both in the office and ambulatory settings. Symptom scores were significantly decreased after 30 and 90 days. This new minimally invasive method appears to be a promising alternative to other treatment methods.

Methods
The prospective study was performed with approval from the IRB. Thirty-two patients with chronic rhinitis and nasal congestion (including allergic and non-allergic rhinitis) who were resistant to medical management were recruited and treated. Patients were treated either in the office under topical/local anesthesia or in an ambulatory center when intranasal anatomy was not favorable and required general anesthesia. Particularly apprehensive, poorly cooperative patients with narrow nasal airway and limited endoscopic visualization to the posterior part of the nose. The Total Nasal Symptom Score (TNSS) was chosen to measure symptom severity and treatment outcomes. The TNSS is the sum of scores for the symptoms of nasal congestion, sneezing, nasal itching, and rhinorrhea at 30 and 90 days following the procedure, using a four point scale (0-3) where 0 indicates no symptoms, 1 indicates mild symptoms that are easily tolerated, 2 is awareness of bothersome but tolerable symptoms, and 3 is reserved for severe, hard to tolerate symptoms that interfere with daily activity. TNSS is calculated by adding the score for each of the symptoms to a total out of 12. Endoscopic laser ablation (ELA) was performed in the office for 11 patients, while the rest were treated under sedation in the operating room. The 940 nm diode laser (Epic-S, Biolase, Irvine, Calif.) with a 400 micron uninitiated malleable fiber tip, which was specially designed for ablation, was pre-shaped and endoscopically advanced toward the posterior middle meatus. The PNN region was ablated by using a continuous wave (CW) at 5 W in a noncontact mode for about 15-20 seconds. Mucosal blanching represented the end of treatment. ELA was performed bilaterally. Patients were followed up for 90 days to assess TNSS. Medication use was also recorded.

Results
All but one patient (96%) were able to complete the procedure. Ten patients were successfully treated in the office and twenty-one in the surgical center. Following procedure, pain was recorded on a 1-10 scale for office-treated patients and was found to be 1.8. No laser safety events were recorded. No crusting, headaches, facial pain, eye dryness, palatal numbness, or ear blockage were recorded at any follow-up visits.

Symptom scores after 30 days showed 55% overall improvement in TNSS. Mean score 7.1 (out of 12) at baseline, was reduced to 3.2. Symptom specific scores showed 48% improvement in rhinorrhea with 53% improvement in nasal congestion after 30 days. Symptom scores 90 days post procedure showed 51% overall improvement in TNSS with symptom-specific scores of 44% improvement in rhinorrhea and 48% improvement in congestion. Total medication use showed 70% reduction in medication use after 90 days. The results were similar in non-allergic 15 (47%) and allergic 17 (53%) patients.

Discussion
In the past, vidian nerve section paved the way to surgical therapy for rhinitis. Ablation of PNN is advantageous for neurectomy considering its feasibility and low complication rate. The recent gain in popularity of cryoablation led to newer studies using alternative technologies to treat the location of the posterior nasal nerves. Studies showed variation in the number and location of the nerves exiting the sphenopalatine (SP) foramen, with up to 20% branching. Furthermore, some authors believe that several small foramina exist alongside the nerves exiting the SP foramen, creating an anastomotic network. The branches of PNN can be found inferior and posterior to the sphenopalatine artery where the middle turbinate attaches to the lateral wall, and by locating the sphenopalatine artery at the sphenopalatine foramen, followed by transaction of a thin periosteum covering from the artery, which allows for clear vision of the nerve and artery.

To date, the only method of PNN surgery in use was direct identification under endoscopic guidance with appropriate nerve section. This method can be considered the gold standard. Histological changes are observed with long-lasting results of up to 48 months in a rat model. Endoscopic PNN section, however, is performed under general anesthesia, is time consuming, and requires meticulous dissection.

Cryotherapy, an ablation method of the PNN region, was developed as early as 1975 and performed with Frigitronics probes (Cooper Surgical, Trumbull, Conn.). The probe reaches −70 C to −90 C and has an effective thermal treatment radius of up to 3-4 mm as the temperature drops to 0 C at a 5 mm radius, with tissue necrosis appearing at the given radius. Common complications included epistaxis, nasal obstruction, nasal crusting, and ear blockage, none of which were reported to be serious. Postoperative bleeding, the most prevalent complication, was readily managed post op with topical therapies in most cases. Efficacy showed overall improvement in symptoms for over 60% of patients, with over 63% improvement in obstructive symptoms and over 77% of patients reporting decreased rhinorrhea. All but one recent study did not quantify the improvement. The only report studying TNSS showed improvement, with TNSS reducing significantly after 30 days (mean±standard deviation: 6.2±0.5 at baseline, 2.6±0.3 at 30 days, n=27, p<0.001) and a continued reduction observed after 90 (2.7±0.4, n=24, p<0.001). The new disposable device is a single-use Clari-Fix device (Arrinex, Redwood City, Calif.), which is inserted into the nose and advanced endoscopically to the target area, then inflated. Likely due to the fact that the inflation was in proximity to the Eustachian tube, most patients felt ear fullness for a week, with an improvement in 74% of patients. The device's disadvantages are its cost and single-location application. Another common side effect is the brain-freeze-type headaches and some mucosal sloughing following the beginning of cryotherapy.

Diode laser PNN ablation as described in this study is a novel method for the management of chronic rhinitis that has failed medical management. As a method in progress, laser PNN ablation showed comparable results to ClariFix and fewer possible complications. The laser has been shown efficacious in the allergic and non-allergic rhinitis groups. Laser ablation enjoys the precision of a malleable fiber tip that can be pre-curved, controlled endoscopically, clearly mapping the PNN target area. In an office setting, the laser fiber can be more economical as a single-use device. In addition, the laser fiber tip can be used for various intranasal procedures, such as turbinate reduction or ablation of swell bodies.

Limitations of the current study include a relatively limited follow-up time. However, predicting from cryotherapy studies, changes beyond three months are limited, and we expect the results to continue to be effective at a later time. These encouraging results merit a larger multicenter study.

CONCLUSION

Laser PNN ablation is safe and well tolerated both in office and in ambulatory settings. Symptom scores were significantly decreased after both 30 and 90 days. This new minimally invasive endoscopic method is a promising alternative to other treatment modalities.

Figure 13:
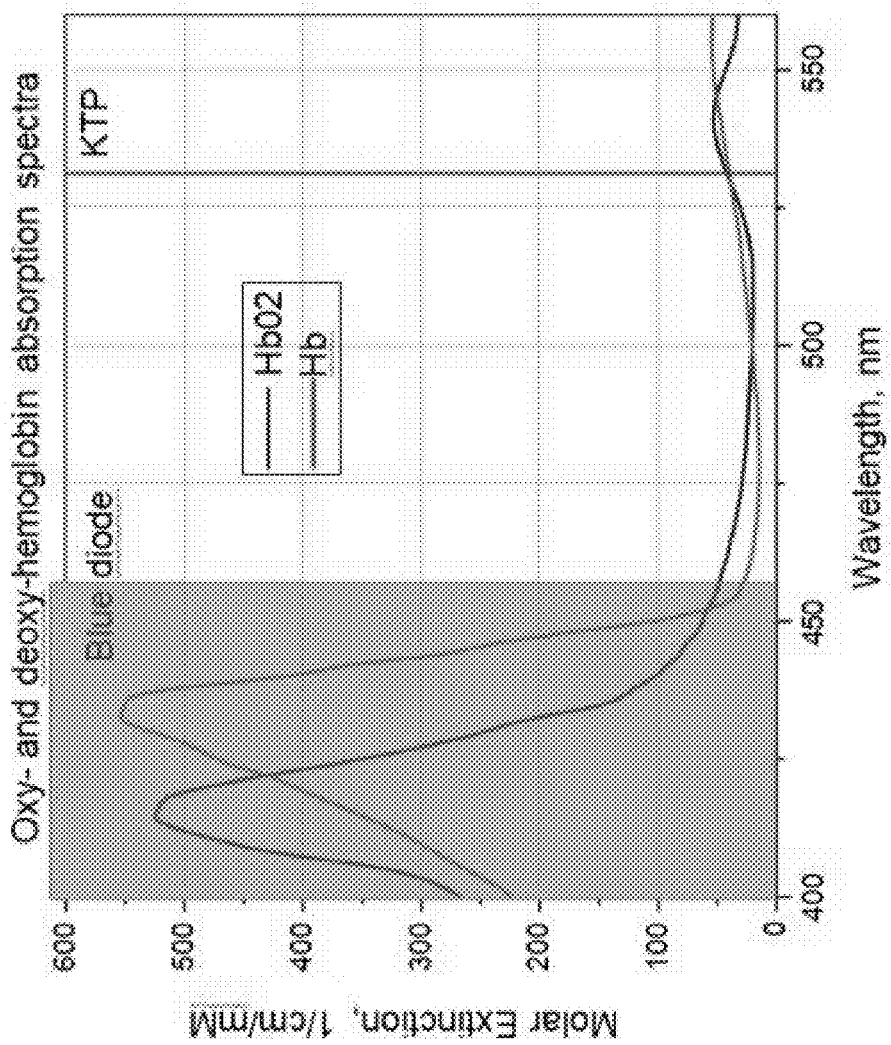
FIG. 13 is a chart of absorption spectra of oxy hemoglobin and deoxyhemoglobin with emission lines.

Another embodiment of the present invention is described now with reference to FIGS. 13 through 17B. In FIG. 13, there is shown a graph of hemoglobin and oxyhemoglobin absorption spectra and also showing emission lines of both KTP lasers and blue diode lasers. Blue light is absorbed by blood, but not by water, and is well suited for treating blood-rich soft tissues such as mucosa. The thermal tissue effect can be tuned in the range from that of potassium titanyl phosphate laser (KTP laser) to approximately five times stronger. A blue laser can cut and coagulate tissue at a distance of greater than 2 mm (like KTP laser) and be used in non-contact mode, which is not possible with electro/mechanical instruments. The blue diode laser also has the advantages of substantially lower cost compared to $CO_2$ laser at the same or approximately the same efficiency level.

Figure 14:
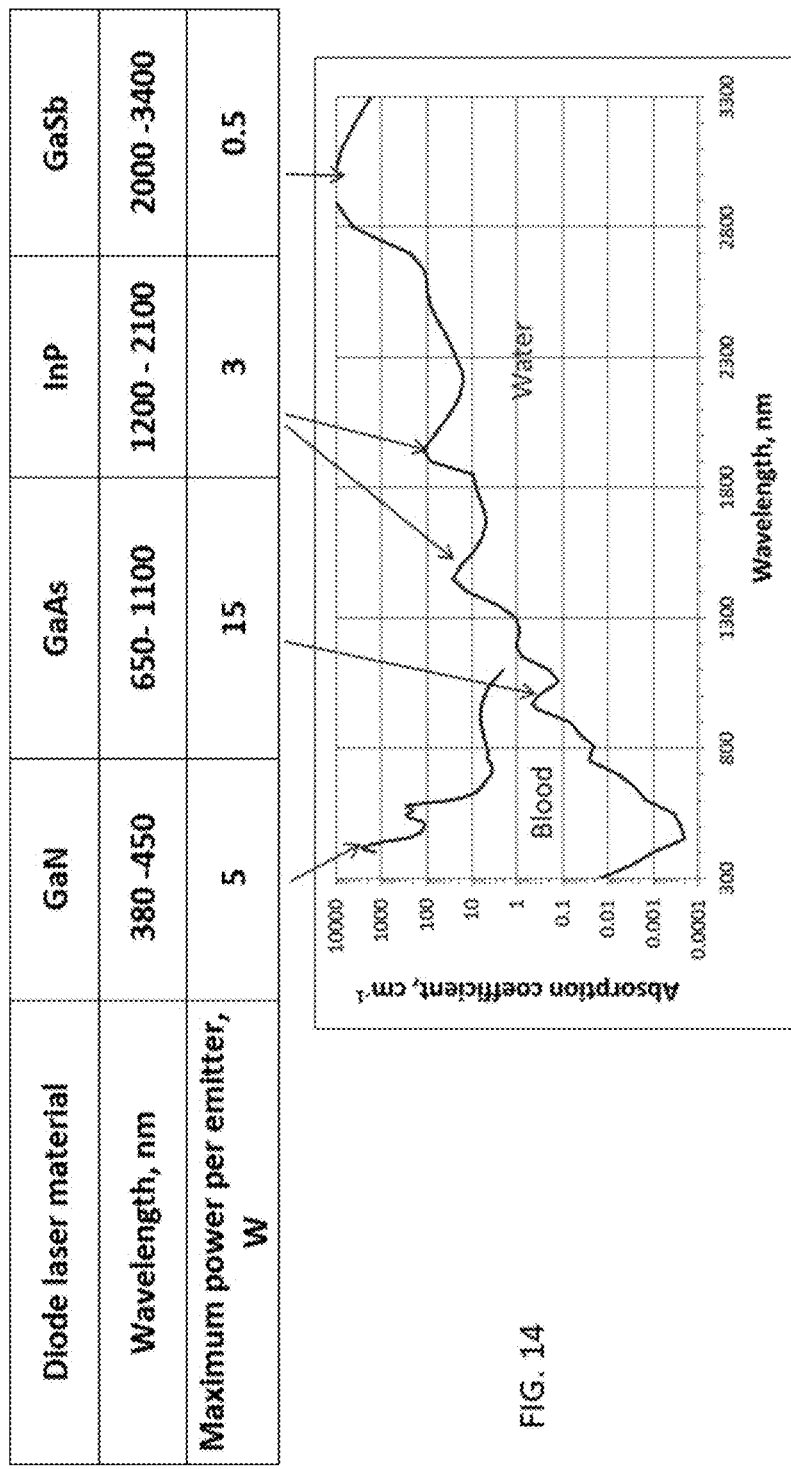
FIG. 14 is a chart of absorption against wavelength for various diode lasers.

With reference now to FIG. 14, there is shown a chart of the low water absorption and high Hgb (blood) absorption typical for blue laser. The blue laser is made by GaN diodes and cover a wavelength range of approximately 380-450 nanometers. Blue lasers have a general range wavelength of 360-480 nanometers and are within the scope of the invention. With FIG. 14, there is illustrated how the wavelength of 380-450 nanometers is best one to use over red colored mucosa and blood vessels of a patient, given the low water absorption and high blood absorption.

Figure 15:
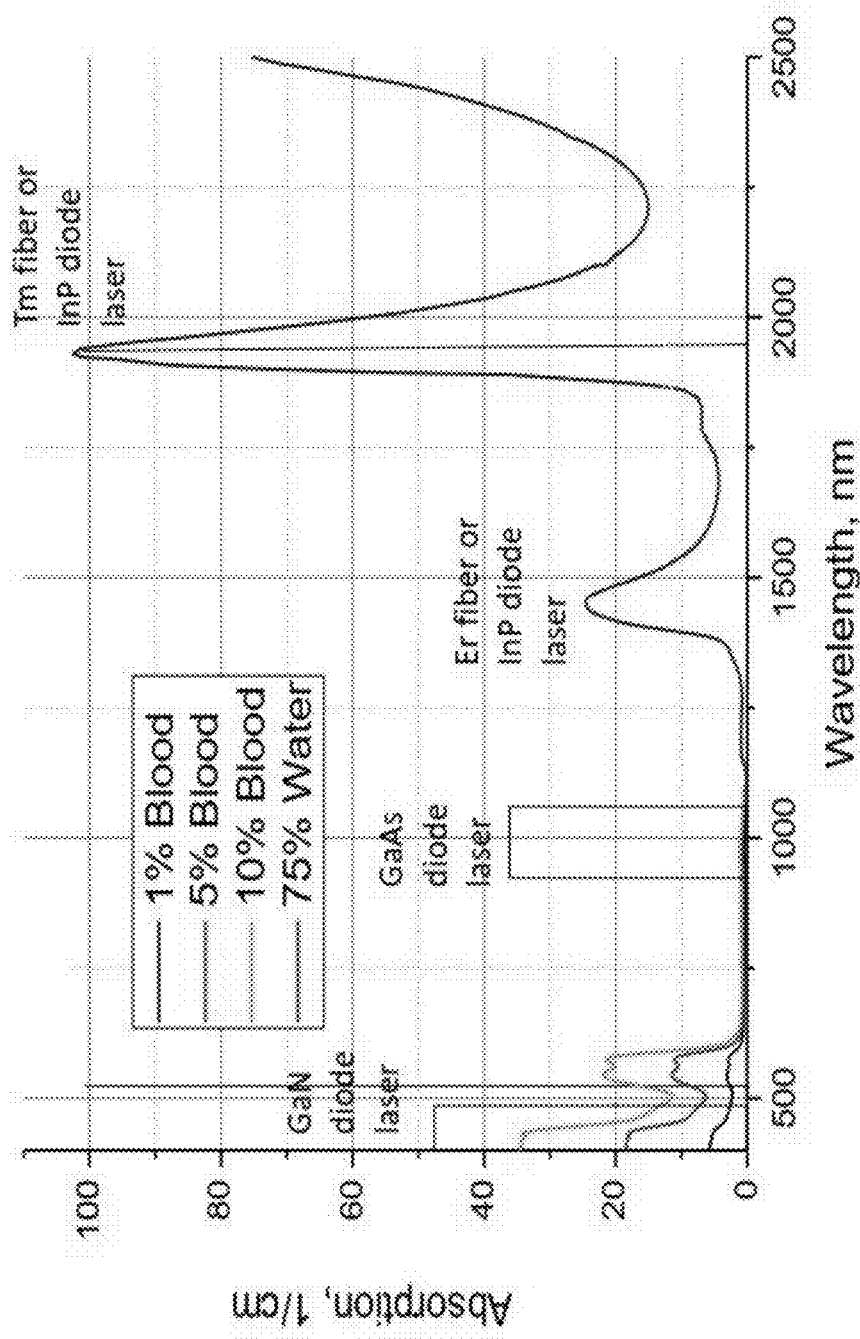
FIG. 15 is a graph of absorption of lasers with silica fiber in soft tissue.

FIG. 15 illustrates a chart of how blue lasers are absorbed with silica fiber in soft tissue. The GaN diode laser absorption is on the left side of the chart with absorption shown for 1% blood, 5% blood, 10% blood, and 75% water. The lasers at 400-500 nm made by GaN diodes are delivered by silica fiber transmitted through soft tissue and blood absorption. There is zero/minimal absorption by water.

The current clinical prototype is as follows: a wavelength of 445 nm is used, with an average power of up to 17 Watts and with a peak power of up to 30 Watts. The GaN blue diode laser (405-450 nm) with coefficient of absorption 10-150 cm−1 can be used for non-contact/focused beam cutting and vaporization similar to $CO_2$ laser in super pulse mode: 10-20 W peak power and 1-10 W average power.

There has been a noted disadvantage of applications of a blue laser according to specialists from Pavlov First Saint Petersburg State Medical University. During the clinical trials one disadvantage of blue laser was discovered—a glass filter must be used to reduce the scattering illumination of the surgical field. Working with a rigid endoscope connected to the camera was therefore practically impossible due to the bright blue light of the emission and the absence of the light filter. It was possible to work only with short single pulses. This is a significant problem as rigid endoscopes are used for most operations in the nasal cavity.

Figure 16A:
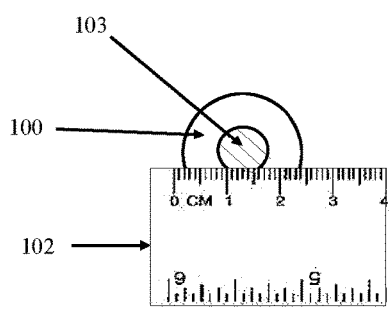
FIGS. 16A and 16B are illustrations of the present invention in use.
Figure 16B:
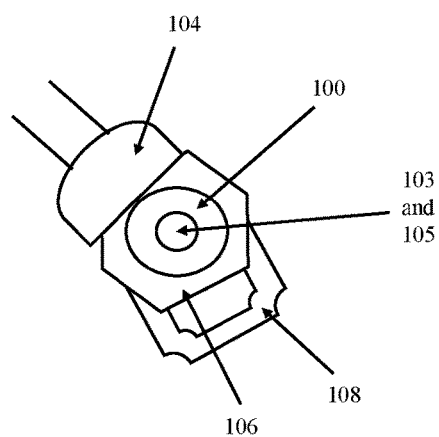

Referring to FIGS. 16A and 16B, there is shown the solution provided with the embodiment of the present invention. The present invention uses an optical filter (for 445 nanometers) of transparent material, glass, polymer etc., that is positioned between the camera and the endoscope in connection with the delivery device described previously. The housing rim 100 with optical filter 103 between is placed between the camera and the endoscope at this position to avoid scattering of the laser beam and to allow the surgeon to clearly see the target area. This present invention is suitable for use with methods and delivery devices described earlier herein. In FIG. 16A there is shown the rim/housing 100 which supports the optical filter 103 (See also FIGS. 17A and 17B), next to a measuring ruler 102 to provide the approximate dimensions, less than one inch (or less than 2.5 cm) outer diameter and less than one centimeter for the inner diameter opening which holds optical filter 103.

In an embodiment, the dimension of the ring housing (the 7 mm filter) should be approximately 3 cm to fit the camera and endoscope assembly showing in FIG. 16B. In FIG. 16B, the rim 100 supporting optical filter 103 is placed over opening 105 within endoscopic camera housing 106 and camera locking system collar 108. The camera locking system 108 keeps the endoscope locked to the camera head. Once the rim 100 with filter 103 is in place so that filter 103 aligns over opening 105, the endoscopic camera housing 106 and camera locking system collar 108 are assembled with the endoscope head piece 104 placed over the assembly. The delivery device described above is connected to the endoscope and camera assembly so the blue laser light is delivered during the medical procedure.

Figure 17A:
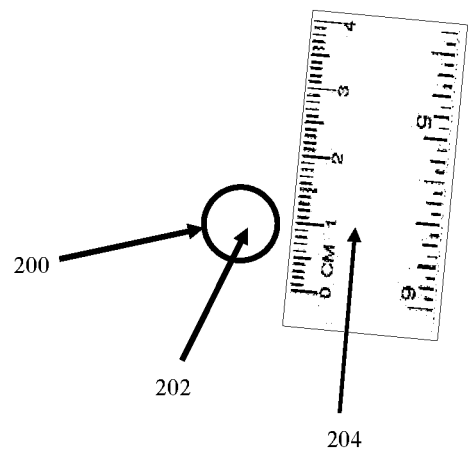
FIGS. 17A and 17B are illustrations of the filter of the present invention.
Figure 17B:
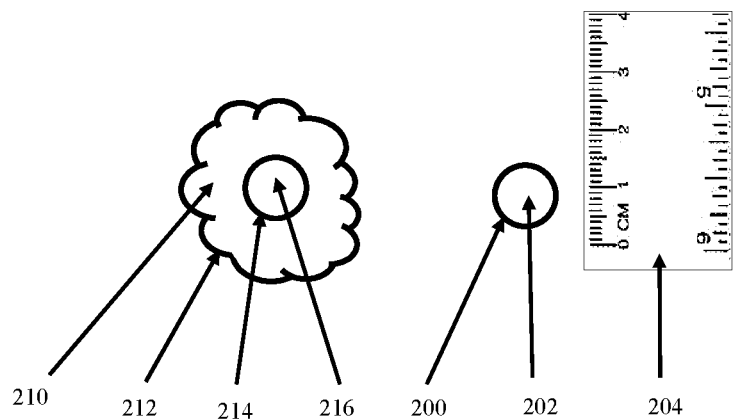

With reference to FIGS. 17A and 17B, there is provided an isolated view of a filter which is used with the present invention. In an embodiment, a 445 nm optical filter was created using a glass filter of approximately 7-8 mm from Omega Optical of Brattleboro, Vt. In FIG. 17A, there is shown the optical filter 200 with glass or optical piece 202 inside the filter and placed next to a ruler 204, which indicates an approximate diameter of less than 1 cm. In FIG. 17B, a handmade housing 210, formed from pressed thick foam, was used to hold the optical filter 200. Metals, composites, plastics, or other suitable materials may be used for the housing. The housing 210 has an outer circumference 212 and an inner circumference 214 defining a center opening 216. The optical filter 200 is placed within foam housing 210 in the center opening 216 where it is held and surrounded by the inner circumference 214. This housing 210 is then placed between the endoscope and the camera head as illustrated before in FIG. 16B. A non-limiting table of specifications of optical filters which may be included for use in the present invention is presented below. Information is provided for the filters as both a light source and as a detector.

|  | Light Source | Detector |
|---|---|---|
| Spectral | | |
| Cut On | 460 nm | 460 nm |
| Peak Transmission - Min. acceptable % | >85% | >85% |
| Attenuation Range - short to long wavelengths | UV-450 nm | UV-450 nm |
| Attenuation OD - short to long wavelengths | OD5 average | OD5 average |
| Physical | | |
| Size/Diameter (mm) | 7.5 + 0/−.25 mm | 9.5 + 0/−.25 mm |
| Thickness: (Max) (mm) | 1.1 +/− 0.1 | 1.1 +/− 0.1 |
| Ring Mounted | unfinished | unfinished |

Figure 17C:
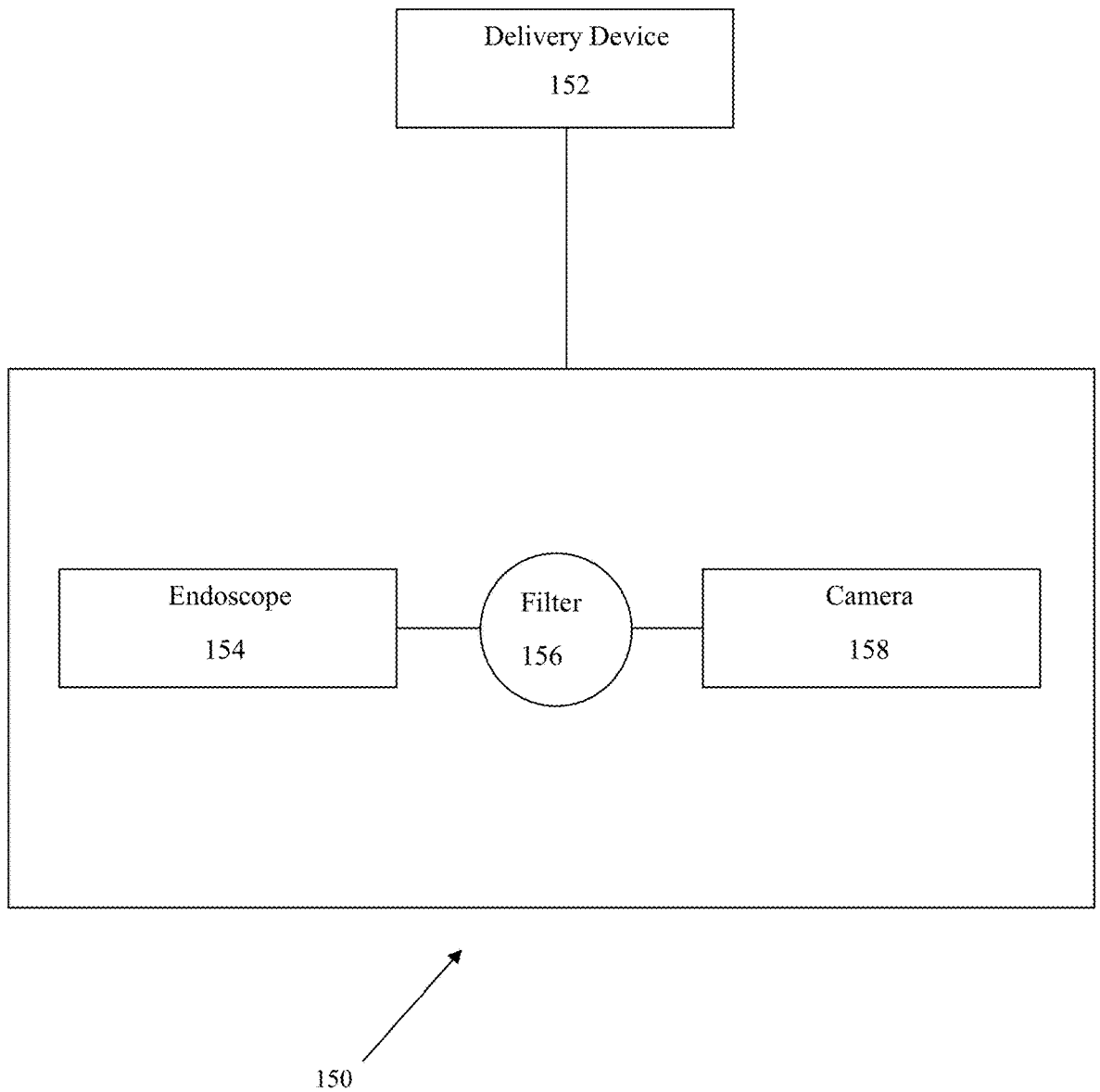
FIG. 17C is a schematic of the overall components of the present invention.

FIG. 17C illustrates the components of the system 150 of the present invention. The filter 156 described above is shown between the endoscope 154 and the camera 158. These are connected with the delivery device 152 described previously for performing the procedures and process of the invention.

With the PNN process specifically performed with a blue laser in the present invention, the medical professional/surgeon can see the blood vessels with the endoscope and since the tiny PNN nerves are running along the blood vessel(s), the surgeon is able to selectively ablate the blood vessels with the blue laser in non-contact coagulation mode. This selective ablation method minimizes the damage, improves the outcome, and is a unique aspect of the blue laser. This is not and cannot be done with other lasers, RF or cryo-based means, or other current methods commercially available. Also, the 940 nm wavelength described herein does not have such selective Hgb absorption characteristics.

With the blue laser, during the process of the invention, the heating of the mucosal surface ideally should be approximately 60-65 Celsius to achieve reversible coagulation effect. Further, the blue laser has temperature feedback control parameters, which is a particular feature to the blue laser. As a result, the laser temporarily shuts off or creates pulsing action (on-off) to maintain the tissue temperature constant until the end of the procedure. The blue laser has superior temperature control on tissue, selectivity to red colored mucosa surface and is highly absorbed by blood Hgb).

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

What is claimed is:

1. A process for the treatment of rhinitis by laser ablation of posterior nasal nerves comprising:
ablating the posterior nasal nerves by a diode laser delivery device with an elongated clear fiber tip, said posterior nasal nerves located above and below a middle turbinate;
said diode laser delivery device inserted into an area of tissue near said middle turbinate;
said laser diode laser delivery device operating at approximately 380 to 450 nanometers;
heating said tissue to approximately 60 to 65 degrees Celsius;
positioning said tip of said diode laser delivery device at a position above said middle turbinate;
ablating lateral posterior superior branches of said posterior nasal nerves;
positioning said tip of said diode laser delivery device at a position below said middle turbinate;
ablating lateral posterior inferior branches of said posterior nasal nerves.

2. The process according to claim 1, wherein said fiber tip of said diode laser delivery device is malleable.

3. The process according to claim 1, wherein the fiber tip of said diode laser delivery device is adjustable and capable of configuration to anatomical differences.

4. The process according to claim 1, wherein said fiber tip is disposable.

5. The process according to claim 1, wherein said diode laser delivery device is re-usable.

6. The process according to claim 1, wherein said diode laser delivery device is disposable.

7. The process according to claim 6, wherein said fiber tip is connected to said disposable diode laser delivery device by removable means.

8. The process according to claim 1, wherein said diode laser delivery device includes a disposable sheath to cover said diode laser delivery device.

9. The process according to claim 1 further comprising selectively ablating blood vessels with a blue laser in a non-contact coagulation mode.

10. The process according to claim 1 wherein said laser diode delivery device operating at approximately 380 to 450 nanometers further comprises an optical filter placed between a camera and an endoscope which are connected to said laser diode delivery device.

11. The process according to claim 1 wherein said laser diode delivery device includes a GaN diode.

\* \* \* \* \*